United States Patent [19]
Haddock et al.

[11] 3,994,713
[45] Nov. 30, 1976

[54] HERBICIDAL ALANINE DERIVATIVES

[75] Inventors: Ernest Haddock, Sheerness; Herbert P. Rosinger, Tunstall, Sittingbourne, both of England

[73] Assignee: Shell Oil Company, Houston, Tex.

[22] Filed: Jan. 6, 1975

[21] Appl. No.: 539,201

[30] Foreign Application Priority Data
Jan. 7, 1974 United Kingdom.................. 677/74

[52] U.S. Cl................................ 71/111; 260/471 A
[51] Int. Cl.².................. A01N 9/20; C07C 103/84
[58] Field of Search.................... 260/471 A; 71/111

[56] References Cited
UNITED STATES PATENTS

| | | |
|---|---|---|
| 3,598,859 | 8/1971 | Yates et al...................... 260/471 A |
| 3,712,805 | 1/1973 | Yates et al........................ 71/111 X |
| 3,761,508 | 9/1973 | Haddock et al. ............... 260/471 A |
| 3,763,216 | 10/1973 | Bertrand......................... 260/471 A |
| 3,780,095 | 12/1973 | Klemm et al. .............. 260/471 A X |

*Primary Examiner*—Richard L. Raymond

[57] ABSTRACT

N,N-disubstituted alanine derivatives of the formula:

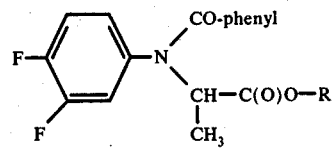

wherein R is $C_1$–$C_3$ alkyl, useful as selective herbicides.

7 Claims, No Drawings

HERBICIDAL ALANINE DERIVATIVES

BACKGROUND OF THE INVENTION

U.S. Pat. No. 3,598,859 describes, inter alia, compounds of the formula

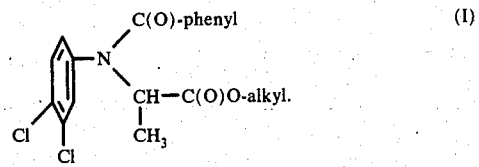

U.S. Pat. No. 3,761,508 describes analogs of the compounds of formula I, wherein the chlorine at the 3-position on the benzene ring is replaced by fluorine, the resulting compounds having the formula:

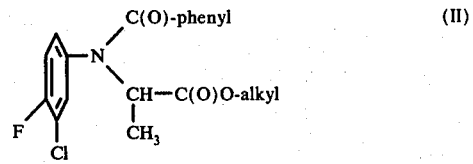

Compounds of formula I were characterized by their selective action in controlling wild oats. Compounds of formula II were characterized by even more selectivity compared to those of formula I in their control of wild oats in cereal crops.

DESCRIPTION OF THE INVENTION

It has been found, and will be demonstrated hereinafter, that analogs of the compounds of formula I wherein both of the chlorine atoms on the benzene ring are replaced by fluorine are unexpectedly even more selective in their action, controlling wild oats in such cereal crops as barley and wheat with even more safety, than the compounds of formula II. The new wild oat herbicides of this invention thus are characterized by the formula

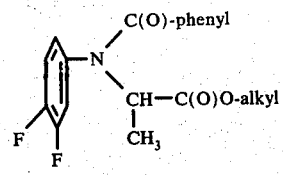

wherein the alkyl moiety contains from 1 to 3 carbon atoms.

The invention also includes a method for inhibiting the growth of wild oats at a locus by applying to the wild oat plants at the locus an effective amount of one or more of the compounds of the invention. Also, because the compounds of the invention are most efficiently marketed and applied in the form of formulations, the invention also includes herbicidal compositions comprising one or more of the compounds of the invention together with an inert carrier, a surface-active agent or both.

The term "carrier" or "inert carrier" as used herein means a material which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating herbicides may be used as carrier.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonates; calcium sulphate; synthetic hydrated silicon oxides and synthetic calcium or aluminum silicates; elements, such as for example, carbon and sulphur; natural and synthetic resins, such as for example, coumarone resins, polyvinyl chloride and styrene polymers and copolymers; solid polychlorophenols; bitumen; waxes, such as for example, beeswax, paraffin wax, and chlorinated mineral waxes; and solid fertilizers, for example, superphosphates.

Examples of suitable fluid carriers are water, alcohols, such as for example, isopropanol and glycols; ketones, such as for example, acetone, methyl ethyl ketone, methyl isobutyl ketone and cyclohexanone; ethers; aromatic hydrocarbons, such as for example, benzene, toluene and xylene; petroleum fractions, such as for example, kerosene, light mineral oils, chlorinated hydrocarbons, such as for example, carbon tetrachloride, perchloroethylene, trichloroethane, including liquefied normally gaseous compounds. Mixtures of different liquids are also suitable.

In addition to a carrier, the present compositions may also contain one or more surface active agents. Suitable surface-active agents include emulsifying agents, dispersing agents or wetting agents. They may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% w of toxicant and usually contain, in addition to solid carrier 3–10% w of a dispersing agent and, where necessary, 0–10% w of stabilizer(s) and/or other additives such as penetrants or stickers. Dusts are usually formulated as a dust concentrate having a similar composition to that of a wettable powder but without a dispersant, and are diluted in the filed with further solid carrier to give a composition usually containing 0.5–10% w of toxicant. Granules are usually prepared to have a size between 10 and 100 BS mesh, and may be manufactured by agglomeration or impregnation techniques. Generally, granules will contain 0.5–25% w toxicant and 0–10% w of additives such as stabilizers, slow-release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents, e.g., bentonites, sodium polyphosphates; stabilizers such as ethylene diamine tetra-acetic acid, urea, triphenyl phosphate; orther herbicides or pesticides; and stickers, for example, non-volatile oils.

Aqueous dispersions and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick "mayonnaise"-like consistency.

The amount of active ingredient(s) necessary to control the wild oats obviously will vary with the individual compound, or mixtures of compounds, used, the type of formulation, the age and condition of the oat plants, environmental conditions and other variable factors which must be and are taken into account by practitioners of the art of chemical control of unwanted plants. Recommendation as to precise dosages therefore is not possible. In general, however, dosages of from about 0.1 to 10 pounds per acre of the active ingredient(s) will be satisfactory. The compounds of the invention cause at most but minor injury to crop plants at the dosages which effectively control wild oats. However, it will be found to be preferable to use the minimum dosage required to effectively control the wild oats, to minimize the possibility of injuring the crop plants significantly. Liquid and dust formulations for such application ordinarily contain from about ½ to about 10% of the active ingredient(s).

The unusual selective activity of compounds of the invention with respect to wild oats growing in cereal crops was demonstrated in the following tests:

25 seeds of barley or wheat or 30 seeds of wild oats were planted in John Innes No. 1 compost contained in 7 cm pots. When the plants had reached the 1½ to 2½ leaf stage, the pots were sprayed with a solution of the test compound in a 1:1 acetone/water mixture containing added wetter/sticker. The crop plants were treated at dosages from 10 to 0.6 kg/ha and the wild oats at dosages from 2.0 to 0.15 kg/ha. Each dosage was replicated four times. The pots were kept in a glasshouse at about 21° C with 16 hours per day of light.

Assessments were made 10–14 days after spraying. The crops were cut at soil level and the plant weight expressed as a percentage of untreated crop weight. The percentage depression in growth of the wild oats was assessed visually. These figures were then used to calculate the growth inhibition dosages and the dosage to give a 10% reduction in growth of the crops ($GID_{10}$) was compared with that to give a 90% reduction in the growth of the wild oats ($GID_{90}$). The selectivity factor for the compound is then given by the expression:

$$\frac{GID_{10} \text{ crop}}{GID_{90} \text{ wild oats}}$$

The compounds of the invention that were tested were:
Ethyl N-benzoyl-N-(3,4-difluorophenyl)-2-aminopropionate (ethyl ester of N-benzoyl-N-(3,4-difluorophenyl)alanine) (Compound A)
Methyl N-benzoyl-N-(3,4-difluorophenyl)-2-aminopropionate (Compound B)
Isopropyl N-benzoyl-N-(3,4-difluorophenyl)-2-aminopropionate (Compound C).

The results of these tests are given in the following table in which there are also included comparative results for the following structurally closely related compounds:
Ethyl N-benzoyl-N-(3-chloro-4-fluorophenyl)-2-aminopropionate (Compound D)
Methyl N-benzoyl-N-(3-chloro-4-fluorophenyl)-2-aminopropionate (Compound E)
Isopropyl N-benzoyl-N-(3-chloro-4-fluorophenyl)-2-aminopropionate (Compound F)

TABLE

Structure: X and Y substituents on a phenyl ring with N bearing C(O)-phenyl and CH(CH₃)—C(O)O—R

| Compound | X | Y | R | $GID_{90}$ (wild oats) | $GID_{10}$ (wheat) | Selectivity Factor (wheat) | $GID_{10}$ (barley) | Selectivity Factor (barley) |
|---|---|---|---|---|---|---|---|---|
| A | F | F | $C_2H_5$ | 0.20 | 1.20 | 6.0 | 0.73 | 3.6 |
| B | F | F | $CH_3$ | 0.21 | 1.67 | 7.9 | 0.96 | 4.5 |
| C | F | F | $CH(CH_3)_2$ | 0.38 | 4.23 | 11.1 | 2.45 | 6.5 |
| D | F | Cl | $C_2H_5$ | 0.12 | 0.50 | 4.2 | 0.27 | 2.3 |
| E | F | Cl | $CH_3$ | 0.12 | 0.53 | 4.4 | 0.33 | 2.7 |
| F | F | Cl | $CH(CH_3)_2$ | 0.30 | 2.33 | 7.7 | 1.44 | 4.7 |

The selectivity factor (S.F.) represents a measure of the selectivity of the compound under test as between the cereal grain and wild oats and the larger the S.F. value, the larger the selectivity of the compound. Thus it will be seen from the above results that when structurally similar esters are compared the compounds of the invention, the latter are significantly more selective than the comparative compounds.

The compounds of the invention can be prepared by treating the appropriate ester of 3,4-difluorophenyl alanine with benzoyl chloride in the presence of a solvent, such as toluene. The precusor esters can be prepared as follows:

Preparation of N-(3,4-difluorophenyl)alanine (1)

A mixture of 120 g of 2-chloropropionic acid, 30 ml of water and 185 g of sodium bicarbonate was added to 140 g of 3,4-difluoroaniline in 50° ml of isopropyl alcohol, and the mixture was refluxed for 24 hours. Further portions of 2-chloropropionic acid and sodium bicarbonate then were added to the stirred mixture until all of the aniline had been converted to the sodium salt of N-(3,4-difluorophenyl)alanine (1A), the reaction being followed by thin layer chromatography of samples of the reaction mixture. Crude 1 was obtained by treating 1A with hydrochloric acid, and then was recrystallized to give 1, m.p.: 163°. The identity and purity of the product was confirmed by nuclear magnetic resonance spectrum (NMR) analysis.

Preparation of the methyl ester (2)

A stirred mixture of 30 g of 1 and 250 ml of dry methanol was saturated with hydrogen chloride. After 3 hours, the reaction mixture was poured into excess sodium bicarbonate solution. The resulting solid material was separated and extracted with methylene chloride. The combined extracts were washed with water and dried over anyhdrous sodium sulfate. The solvent was evaporated and the residue was crystallized from ice-cold hexane to give 2, m.p.: 32°. The identity of purity of the product was confirmed by NMR analysis.

The ethyl ester (3, m.p.: 26°) and the isopropyl ester (4, m.p.: 34°) were prepared by the same procedure from the corresponding alcohols, the identity of purity of each product being confirmed by NMR analysis.

Preparation of Compound A 4.2 g of 3 and 2.81 g of benzoyl chloride in 50 ml of dry toluene were heated together under reflux for 6 hours. The solvent then was evaporated under reduced pressure and the residue purified by chromatography on alumina using as eluent a 1:2 mixture of benzene and hexane to give Compound A as a colorless crystalline solid, m.p.: 60°, identity confirmed by NMR analysis.

Compound B was obtained as a colorless crystalline solid, m.p.: 80°, and Compound C was obtained as a colorless crystalline solid, m.p.: 52°, by treating 2 and 4, respectively, with benzoyl chloride by the procedure used for preparation and separation of Compound A. The identities of the products were confirmed by NMR analyses.

I claim as my invention:

1. A compound of the formula:

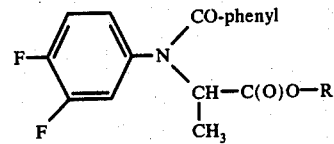

wherein R is $C_1$–$C_3$ alkyl.

2. A compound according to claim 1 wherein R is isopropyl.
3. A compound according to claim 1 wherein R is methyl.
4. A compound according to claim 1 wherein R is ethyl.
5. A herbicidal composition comprising a herbicidally effective amount of a compound according to claim 1, together with a carrier, a surface active agent or both a carrier and a surface active agent.
6. A method of combating the growth of wild oats at a locus by applying to the locus a herbicidally effective amount of a composition according to claim 5.
7. A method according to claim 6 wherein the composition as applied as a post-emergent application to a wheat or barley crop infested with growing wild oat plants.

* * * * *